(12) United States Patent
Murase et al.

(10) Patent No.: US 10,835,109 B2
(45) Date of Patent: Nov. 17, 2020

(54) ENDOSCOPE SYSTEM

(71) Applicant: Sony Olympus Medical Solutions Inc., Tokyo (JP)

(72) Inventors: Hirofumi Murase, Tokyo (JP); Takahiro Yamamoto, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/164,062

(22) Filed: Oct. 18, 2018

(65) Prior Publication Data

US 2019/0167080 A1    Jun. 6, 2019

(30) Foreign Application Priority Data

Dec. 1, 2017 (JP) .................. 2017-232157

(51) Int. Cl.
| A61B 1/00 | (2006.01) |
| A61B 1/06 | (2006.01) |
| G02B 23/24 | (2006.01) |
| A61B 1/05 | (2006.01) |
| A61B 1/04 | (2006.01) |
| A61B 1/045 | (2006.01) |
| H04N 5/225 | (2006.01) |

(52) U.S. Cl.
CPC ...... *A61B 1/00163* (2013.01); *A61B 1/00009* (2013.01); *A61B 1/00096* (2013.01); *A61B 1/00188* (2013.01); *A61B 1/042* (2013.01); *A61B 1/045* (2013.01); *A61B 1/05* (2013.01); *A61B 1/0676* (2013.01); *G02B 23/2461* (2013.01); *A61B 1/00066* (2013.01); *G02B 23/2484* (2013.01); *H04N 2005/2255* (2013.01)

(58) Field of Classification Search
CPC combination set(s) only.
See application file for complete search history.

(56) References Cited

U.S. PATENT DOCUMENTS

| 2009/0245600 | A1* | 10/2009 | Hoffman | H04N 13/366 382/128 |
| 2012/0262559 | A1* | 10/2012 | On | H04N 5/23267 348/65 |
| 2014/0376792 | A1* | 12/2014 | Matsuzaki | A61B 1/00009 382/128 |
| 2016/0234427 | A1* | 8/2016 | Yoshino | A61B 1/00036 |
| 2017/0100018 | A1* | 4/2017 | Saito | A61B 1/00 |

FOREIGN PATENT DOCUMENTS

JP    2015-134039    7/2015

* cited by examiner

*Primary Examiner* — Janese Duley
(74) *Attorney, Agent, or Firm* — Xsensus LLP

(57) ABSTRACT

An endoscope system includes: an imaging device detachably connected to an eyepiece unit of an endoscope inserted into a subject, the endoscope taking a subject image inside the subject from a distal end thereof, and the imaging device being configured to capture the subject image taken by the endoscope; a detection area setting unit configured to set a detection area in the captured image captured by the imaging device; a detection processing unit configured to execute, based on an image in the detection area in the captured image, a detection process for calculating an evaluation value of the image; and a subject image determining unit configured to determine a size of the subject image in the captured image, wherein the detection area setting unit changes an area of the entire detection area based on a determination result of the subject image determining unit.

18 Claims, 9 Drawing Sheets

FIG.3
(a)
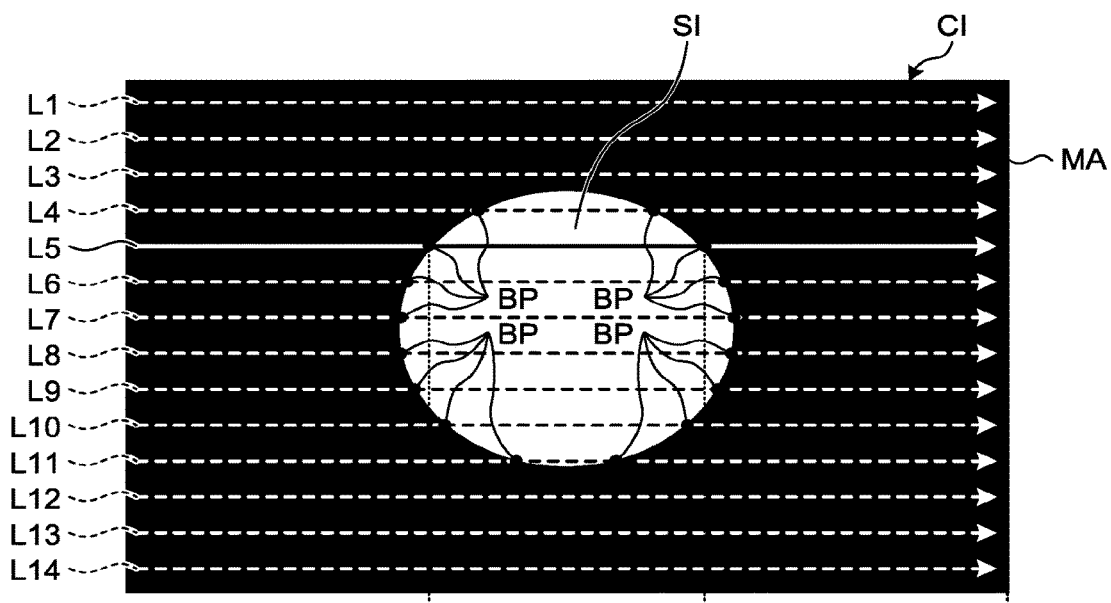
(b)
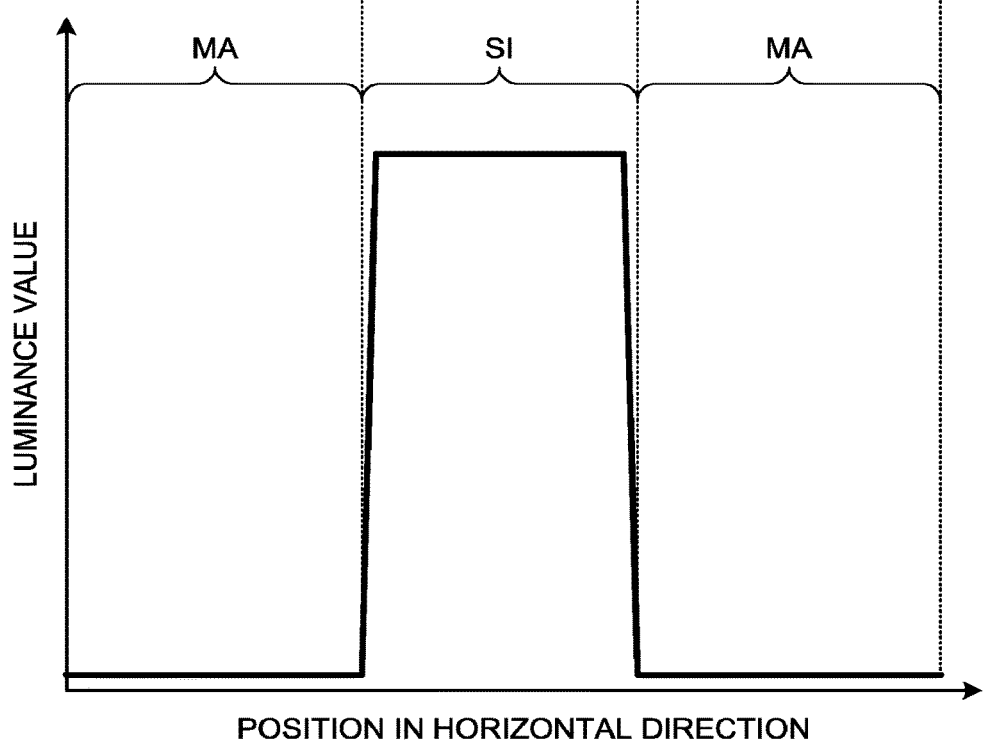

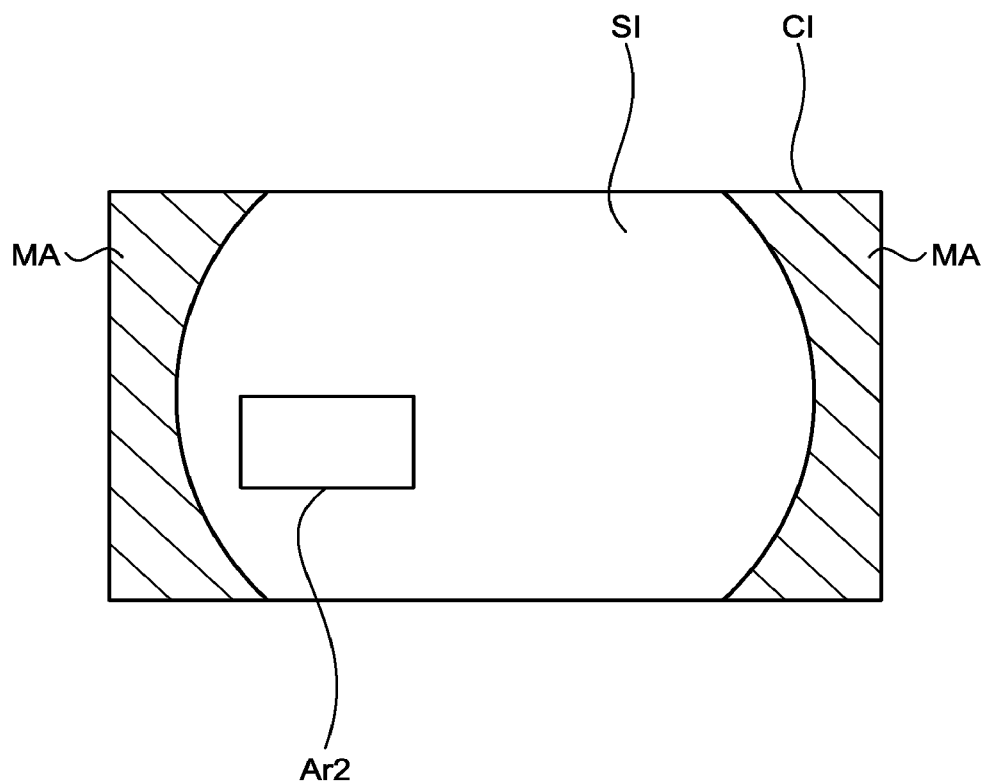

… (1)

ENDOSCOPE SYSTEM

CROSS-REFERENCE TO RELATED APPLICATION(S)

The present application claims priority to and incorporates by reference the entire contents of Japanese Patent Application No. 2017-232157 filed in Japan on Dec. 1, 2017.

BACKGROUND

The present disclosure relates to an endoscope system.

In the past, endoscope systems for observing an inside of a subject such as a person or a machine structure have been known (for example, see JP 2015-134039 A).

The endoscope system (endoscope device) disclosed in JP 2015-134039 A includes an imaging device (camera head), a control device, and a display device. Here, the imaging device is detachably connected to an eyepiece unit of an endoscope (insertion unit) which is inserted into the subject and takes a subject image in the subject from a distal end, and captures the subject image taken by the endoscope. Further, the control device processes the captured image captured by the imaging device and generates a video signal for display. Further, the display device displays an image based on the video signal generated by the control device. Further, the imaging device includes a lens unit configured to be movable in an optical axis direction and a driving motor for causing the lens unit to move along an optical axis. Further, in the endoscope system disclosed in JP 2015-134039 A, the subject image in the captured image may be set to a focused state (manually focusable) by changing a position (focus position) of the lens unit.

SUMMARY

By the way, in the endoscope system disclosed in JP 2015-134039 A, in a case in which a so-called autofocus (AF) function is provided, it is considered to be configured as follows.

In other words, in the captured image, a detection area is set in some areas including a center position. Further, a detection process for calculating an evaluation value of the image is executed based on an image in the detection area. Then, the evaluation value is calculated based on a result of the detection process, and the focus position is adjusted to a focus position at which the subject image in the detection area becomes the focused state in accordance with the evaluation value.

FIGS. 9A and 9B are diagrams for describing a problem in an endoscope system according to a related art. Specifically, FIG. 9A illustrates a captured image CI captured by an imaging device in a state in which an endoscope having a large diameter is connected to the imaging device. FIG. 9B illustrates a captured image CI captured by an imaging device in a state in which an endoscope having a small diameter is connected to the imaging device.

Here, a size of a subject image SI in the captured image CI varies depending on a diameter size of the endoscope connected to the imaging device. Specifically, the size of the subject image SI (FIG. 9A) when the endoscope having a large diameter is connected to the imaging device is larger than the size of the subject image SI (FIG. 9B) when the endoscope having a small diameter is connected to the imaging device. In FIGS. 9A and 9B, masked areas MA other than the subject image SI are hatched in the captured image CI.

Further, a detection area $Ar0$ is considered to be set to a size corresponding to the size of the subject image SI (FIG. 9B) when the endoscope having the smallest diameter among the endoscopes connected to the imaging device is connected as illustrated in FIGS. 9A and 9B. However, in a case in which the detection area $Ar0$ is set when the endoscope having a large diameter is connected to the imaging device, the detection area $Ar0$ is much smaller than the subject image SI as illustrated in FIG. 9A. Further, in a case in which the detection area $Ar0$ is an extremely small area, a treatment tool such as electric scalpel, gauze, or the like is likely to enter (be shown in) the entire detection area $Ar0$. As described above, when the treatment tool such as the electric scalpel, the gauze, or the like enters the entire detection area $Ar0$, accuracy of the evaluation value calculated based on the detection process result (hereinafter referred to as "detection accuracy") deteriorates, and as a result, there is a problem in that a part of interest to be observed is unable to become the focused state.

In this regard, there is a demand for a technique capable of obtaining constant detection accuracy even in a case in which various endoscopes having different diameter sizes are used.

An endoscope system according to one aspect of the present disclosure includes: an imaging device detachably connected to an eyepiece unit of an endoscope inserted into a subject, the endoscope taking a subject image inside the subject from a distal end thereof, and the imaging device being configured to capture the subject image taken by the endoscope; a detection area setting unit configured to set a detection area in the captured image captured by the imaging device; a detection processing unit configured to execute, based on an image in the detection area in the captured image, a detection process for calculating an evaluation value of the image; and a subject image determining unit configured to determine a size of the subject image in the captured image, wherein the detection area setting unit changes an area of the entire detection area based on a determination result of the subject image determining unit.

BRIEF DESCRIPTION OF THE DRAWINGS

FIG. 3 is a diagram for describing a mask edge detection process;

FIG. 7 is a diagram illustrating a modified example of the first and second embodiments;

DETAILED DESCRIPTION

Figure 1:
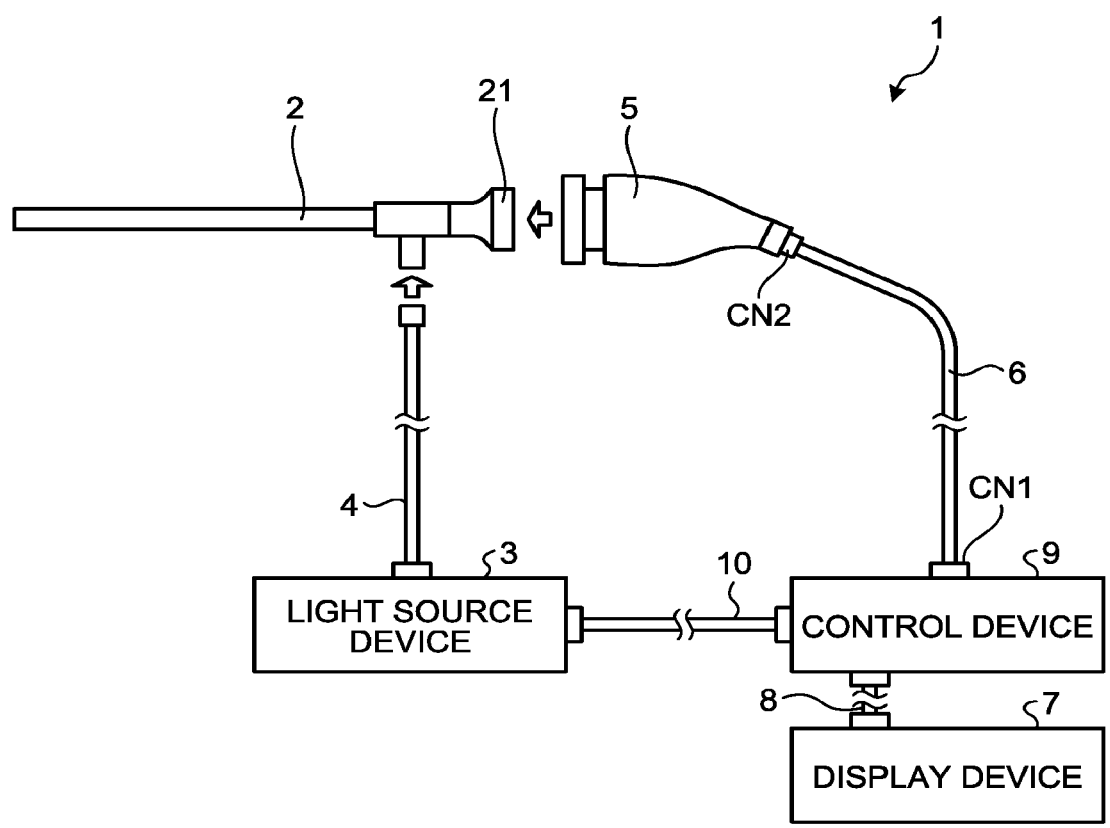
FIG. 1 is a diagram illustrating a schematic configuration of an endoscope system according to a first embodiment.

Hereinafter, modes (hereinafter, embodiments) for carrying out the present disclosure will be described with reference to the appended drawings. The present disclosure is not limited by the embodiments to be described below. Further, in the description of the drawings, the same reference numerals are assigned to the same parts.

First Embodiment

Schematic Configuration of Endoscope System

FIG. 1 is a diagram illustrating a schematic configuration of an endoscope system 1 according to the first embodiment.

The endoscope system 1 is used in a medical field and is a device for observing a living object. As illustrated in FIG. 1, the endoscope system 1 includes an endoscope 2, a light source device 3, a light guide 4, a camera head 5, a first transmission cable 6, a display device 7, a second transmission cable 8, a control device 9, and a third transmission cable 10.

The endoscope 2 is a rigid endoscope. In other words, the endoscope 2 has an elongated shape which is rigid or at least partly flexible and is inserted into a living object. An optical system which is constituted using one or more lenses and condenses a subject image is installed inside the endoscope 2.

The light source device 3 is connected to one end of the light guide 4 and supplies light for illuminating the inside of the living object to one end of the light guide 4 under the control of the control device 9.

One end of the light guide 4 is detachably connected to the light source device 3, and the other end thereof is detachably connected to the endoscope 2. The light guide 4 transmits the light supplied from the light source device 3 from one end to the other end and supplies the light to the endoscope 2. The light supplied to the endoscope 2 is emitted from a distal end of the endoscope 2 and is radiated to the inside of the living object. The light (subject image) radiated to the inside of the living object and reflected inside the living object is condensed by the optical system in the endoscope 2.

The camera head 5 corresponds to an imaging device according to the present disclosure. The camera head 5 is detachably connected to a proximal end (an eyepiece unit 21 (FIG. 1)) of the endoscope 2. Under the control of the control device 9, the camera head 5 captures the subject image condensed by the endoscope 2 and outputs an image signal (RAW signal) by the imaging. The image signal is, for example, an image signal of 4 K or more. A detailed configuration of the camera head 5 will be described later.

One end of the first transmission cable 6 is detachably connected to the control device 9 via a connector CN1 (FIG. 1), and the other end thereof is detachably connected to the camera head 5 via a connector CN2 (FIG. 1). Further, the first transmission cable 6 transmits the image signal or the like output from the camera head 5 to the control device 9, and transmits a control signal, a synchronization signal, a clock, electric power, and the like output from the control device 9 to the camera head 5.

The transmission of the image signal or the like from the camera head 5 to the control device 9 via the first transmission cable 6 may be performed by transmitting the image signal or the like using an optical signal or an electric signal. The same applies to the transmission of the control signal, the synchronization signal, and the clock from the control device 9 to the camera head 5 via the first transmission cable 6.

The display device 7 is constituted using a display using liquid crystal, organic electro luminescence (EL), or the like, and displays an image based on a video signal from the control device 9 under the control of the control device 9.

One end of the second transmission cable 8 is detachably connected to the display device 7, and the other end thereof is detachably connected to the control device 9. Further, the second transmission cable 8 transmits the video signal processed by the control device 9 to the display device 7.

The control device 9 includes a central processing unit (CPU) and the like, and controls the operations of the light source device 3, the camera head 5, and the display device 7 in general. A detailed configuration of the control device 9 will be described later.

One end of the third transmission cable 10 is detachably connected to the light source device 3, and the other end thereof is detachably connected to the control device 9. Further, the third transmission cable 10 transmits the control signal from the control device 9 to the light source device 3.

Configuration of Camera Head

Next, a configuration of the camera head 5 will be described.

Figure 2:
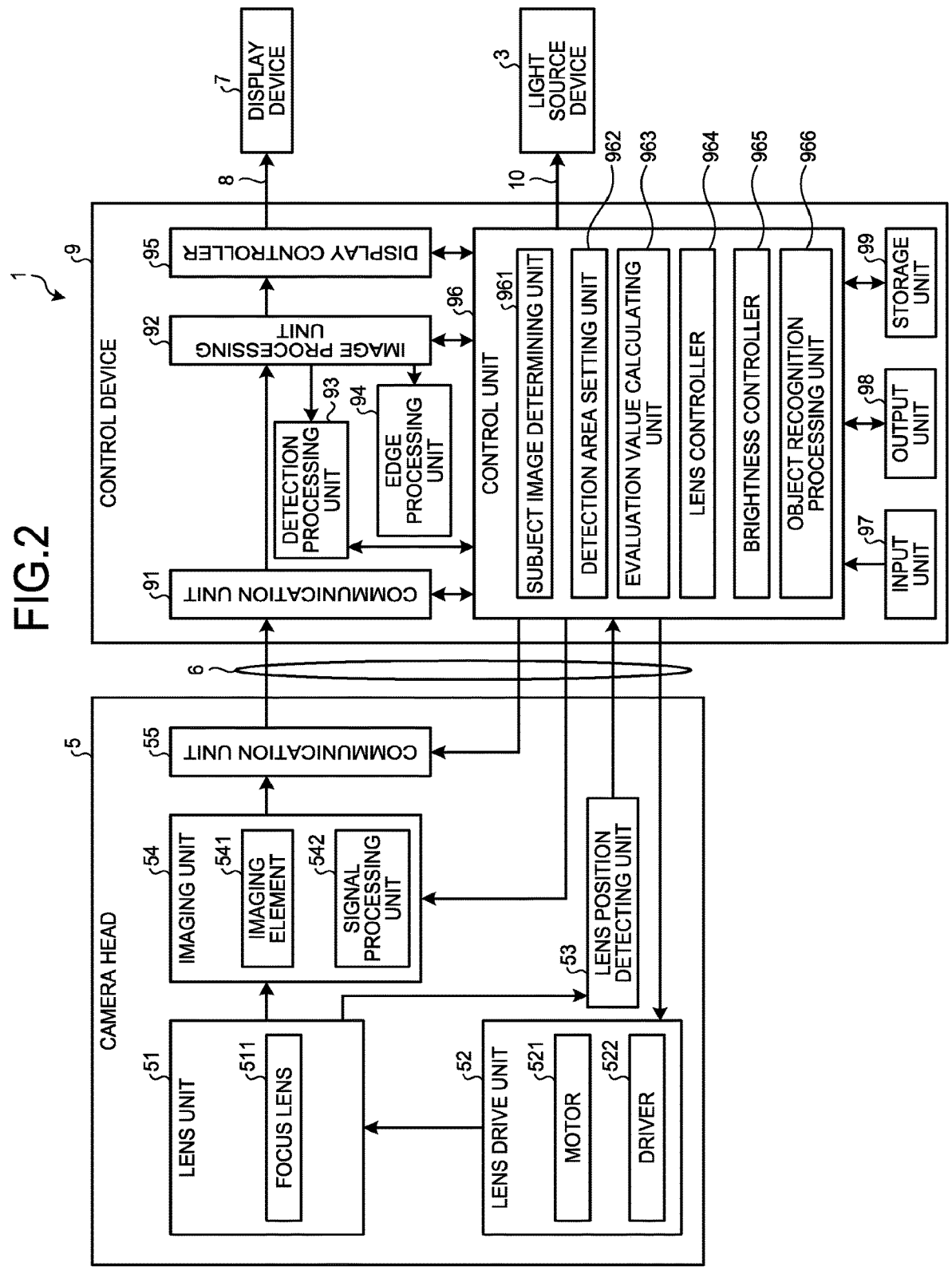
FIG. 2 is a block diagram illustrating configurations of a camera head and a control device.

FIG. 2 is a block diagram illustrating configurations of the camera head 5 and the control device 9.

For the sake of convenience of description, the connectors CN1 and CN2 between the control device 9 and the camera head 5 and the first transmission cable 6, a connector between the control device 9 and the second transmission cable 8, a connector between the display device 7 and the second transmission cable 8, a connector between the control device 9 and the third transmission cable 10, and a connector between the light source device 3 and the third transmission cable 10 are not illustrated in FIG. 2.

As illustrated in FIG. 2, the camera head 5 includes a lens unit 51, a lens drive unit 52, a lens position detecting unit 53, an imaging unit 54, and a communication unit 55.

The lens unit 51 is constituted using a plurality of lenses which are movable along an optical axis, and the subject image condensed by the endoscope 2 is formed on an imaging plane of the imaging unit 54 (an imaging element 541 (FIG. 2)). As illustrated in FIG. 2, the lens unit 51 includes a focus lens 511.

The focus lens 511 is constructed using one or more lenses and moves along the optical axis to adjust a focal point.

A focus mechanism (not illustrated) that causes the focus lens 511 to move along the optical axis is installed in the lens unit 51.

As illustrated in FIG. 2, the lens drive unit 52 includes a motor 521 that operates the focus mechanism and a driver 522 that drives the motor 521. Further, the lens drive unit 52 adjusts the focal point of the lens unit 51 under the control of the control device 9.

The lens position detecting unit 53 is constituted using a position sensor such as a photo interrupter and detects a lens position of the focus lens 511 (hereinafter referred to as a focus position). Then, the lens position detecting unit 53 outputs a detection signal corresponding to the focus position to the control device 9 via the first transmission cable 6.

Under the control of the control device 9, the imaging unit 54 images the inside of the living object. As illustrated in FIG. 2, the imaging unit 54 includes an imaging element 541 and a signal processing unit 542.

The imaging element 541 is constituted by a charge coupled device (CCD), a complementary metal oxide semiconductor (CMOS), or the like which receives the subject image which is condensed by the endoscope 2 and formed by the lens unit 51 and converts the subject image into an electrical signal (analog signal).

The signal processing unit 542 performs signal processing on the electric signal (analog signal) from the imaging element 541 and outputs an image signal (RAW signal (digital signal)).

For example, the signal processing unit 542 performs signal processing such as a process of removing reset noise, a process of multiplying an analog gain for amplifying the analog signal, and A/D conversion on the electric signal (analog signal) from the imaging element 541.

The communication unit 55 functions as a transmitter that transmits the image signal (RAW signal (digital signal)) output from the imaging unit 54 to the control device 9 via the first transmission cable 6. The communication unit 55 is constituted by, for example, a high-speed serial interface which performs communication of the image signal with the control device 9 via the first transmission cable 6 at a transmission rate of 1 Gbps or more.

Configuration of Control Device

Next, a configuration of the control device 9 will be described with reference to FIG. 2.

As illustrated in FIG. 2, the control device 9 includes a communication unit 91, an image processing unit 92, a detection processing unit 93, an edge processing unit 94, a display controller 95, a control unit 96, an input unit 97, an output unit 98, and a storage unit 99.

The communication unit 91 functions as a receiver that receives the image signal (RAW signal (digital signal)) output from the camera head 5 (the communication unit 55) via the first transmission cable 6. The communication unit 91 is constituted by, for example, a high-speed serial interface that performs communication of the image signal with the communication unit 55 at a transmission rate of 1 Gbps or more.

The image processing unit 92 processes the image signal (RAW signal (digital signal)) which is output from the camera head 5 (communication unit 55) and received by the communication unit 91 under the control of the control unit 96.

For example, the image processing unit 92 multiplies the image signal (RAW signal (digital signal)) by a digital gain for amplifying the digital signal. Further, the image processing unit 92 performs RAW processing such as an optical black subtraction process and a demosaic process on the image signal (RAW signal (digital signal)) multiplied by the digital gain and converts the RAW signal (image signal) into an RGB signal (image signal). Further, the image processing unit 92 performs RGB processing such as a white balance adjustment process of multiplying each RGB value by a gain, RGB gamma correction, and YC conversion (conversion of the RGB signal into a luminance signal and a color difference signal (Y and $C_B/C_R$ signals)) on the RGB signal (image signal). Further, the image processing unit 92 performs YC processing such as color difference correction and noise reduction on the Y and $C_B/C_R$ signals (the image signal). Further, the image processing unit 92 executes a shake compensation process of correcting movement of the subject caused by camera shaking (a process of moving an image by an "evaluation value (deviation amount) for the shake compensation process" calculated by an evaluation value calculating unit 963 to be described later) on the image signal (the Y and $C_R/C_R$ signals) which has undergone the YC processing.

The detection processing unit 93 receives the image signal (Y and $C_B/C_R$ signals or RGB signal) processed by the image processing unit 92, and executes the detection process based on the image signal (the Y and $C_B/C_R$ signals or the RGB signal).

For example, the detection processing unit 93 executes detection of a contrast and a frequency component of an image in a detection area, detection of an average luminance value or maximum and minimum pixels in the detection area by a filter, comparison determination with a threshold value, and detection of a histogram based on pixel information (for example, a luminance signal (the Y signal)) of each pixel in the detection area which is some areas of the entire captured image of one frame captured by the imaging element 541. Then, the detection processing unit 93 outputs the detection information obtained by the detections (the contrast, the frequency component, the average luminance value, the maximum and minimum pixels, the histogram, and the like) to the control unit 96.

The edge processing unit 94 executes a mask edge detection process based on the luminance signal (the Y signal) constituting the image signal (the Y and $C_B/C_R$ signals) processed by the image processing unit 92.

FIG. 3 is a diagram for describing the mask edge detection process. More specifically, a part (a) of FIG. 3 is a diagram illustrating an example of a captured image CI captured by the imaging element 541. A part (b) of FIG. 3 is a diagram illustrating a distribution of luminance values in a horizontal line L5 in the captured image CI illustrated in the part (a) of FIG. 3.

Here, the light (subject image) which is reflected inside the living object and condensed in the endoscope 2 has a substantially circular cross section. For this reason, the subject image SI in the captured image CI is substantially circular as illustrated in the part (a) of FIG. 3. In other words, the captured image CI includes a subject image SI and a mask area MA other than the subject image SI. In the part (a) of FIG. 3, the mask area MA is colored with black.

The edge processing unit 94 detects a boundary point BP (the part (a) of FIG. 3) between the subject image SI and the mask area MA by executing the mask edge detection process.

Specifically, as illustrated in the part (a) of FIG. 3, the edge processing unit 94 acquires the luminance signal (Y signal) of the image signal (Y and $C_B/C_R$ signals) processed by the image processing unit 92. Then, based on the luminance signal (Y signal), the edge processing unit 94 detects distributions of the luminance values in a plurality of horizontal lines (14 horizontal lines L1 to L14 in the example of the part (a) of FIG. 3) in the captured image CI based on the luminance signal (the Y signal). Here, in the captured image CI, the area of the subject image SI is higher in the luminance value than the mask area MA. In other words, for example, in the luminance distribution in the horizontal line L5, the luminance value is high between the two boundary points BP of the subject image SI and the mask area MA, and the luminance value is low in the other parts as illustrated in the part (b) of FIG. 3. Therefore, the edge processing unit 94 recognizes a position at which the luminance value changes on the horizontal line as the boundary point BP. Further, the edge processing unit 94 recognizes a plurality of boundary points BP between the subject image SI and the mask area MA by executing the above process on all the horizontal lines. Then, the edge processing unit 94 outputs signals corresponding to a plurality of recognized boundary points BP (pixel positions (coordinate values)) to the control unit 96.

Under the control of the control unit 96, the display controller 95 generates a video signal for display based on the image signal (Y and $C_B/C_R$ signals) processed by the image processing unit 92. Then, the display controller 95 outputs the video signal to the display device 7 via the second transmission cable 8.

The control unit 96 is constituted using, for example, a CPU or the like and outputs the control signals via the first to third transmission cables 6, 8, and 10 to control the operations of the light source device 3, the camera head 5, and the display device 7 and control the overall operation of the control device 9. As illustrated in FIG. 2, the control unit 96 includes a subject image determining unit 961, a detection area setting unit 962, an evaluation value calculating unit 963, a lens controller 964, a brightness controller 965, and an object recognition processing unit 966.

Based on a plurality of boundary points BP (pixel positions (coordinate values)) recognized by the edge processing unit 94, the subject image determining unit 961 recognizes the subject image SI (pixel positions (coordinate values)) surrounded by a plurality of boundary points BP and determines the size of the subject image SI (for example, the diameter of the subject image SI).

The detection area setting unit 962 executes a detection area setting process for setting the detection area in the detection process by the detection processing unit 93 based on the determination result by the subject image determining unit 961.

Figure 4A:
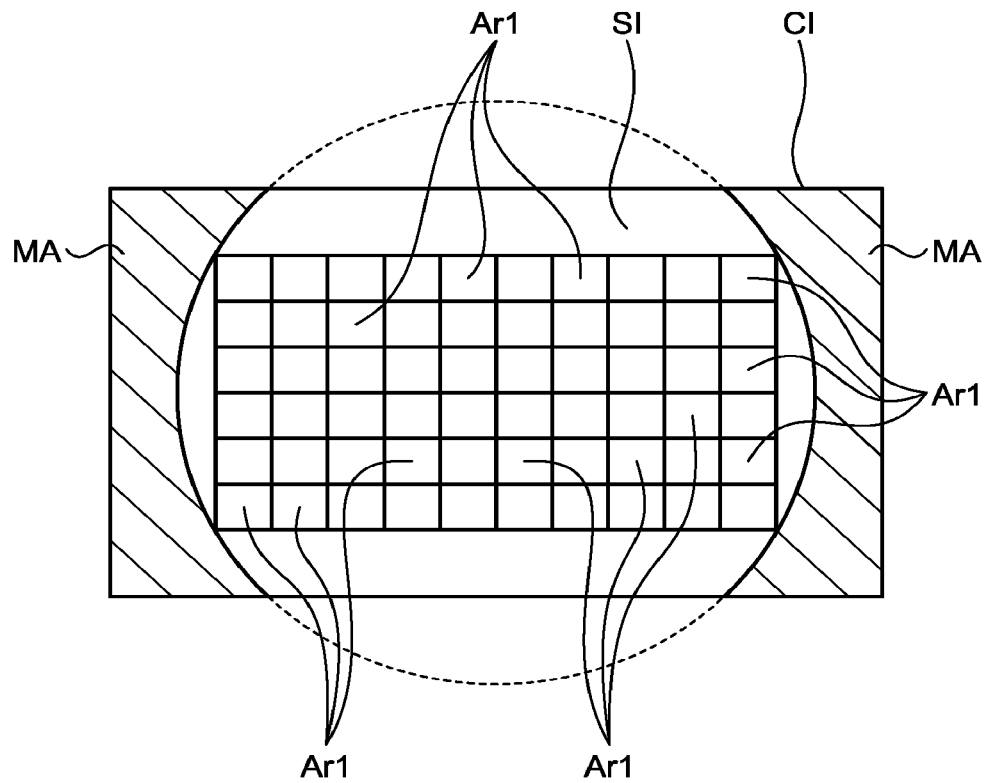
FIG. 4A is a diagram for describing a detection area setting process.
Figure 4B:
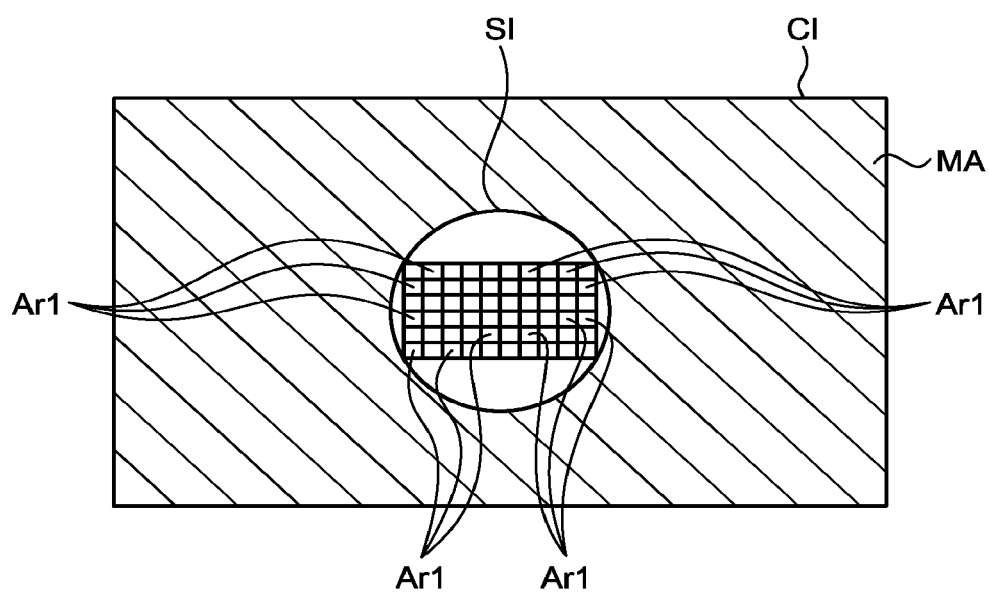
FIG. 4B is a diagram for describing a detection area setting process.

FIGS. 4A and 4B are diagrams for describing the detection area setting process. Specifically, FIG. 4A illustrates the captured image CI captured by the imaging unit 54 in a state in which the endoscope 2 having a large diameter is connected to the camera head 5. FIG. 4B illustrates the captured image CI captured by the imaging unit 54 in a state in which endoscope 2 having a small diameter is connected to the camera head 5.

Here, the size of the subject image SI varies depending on the diameter size of the endoscope 2 connected to the camera head 5. Specifically, the size of the subject image SI (FIG. 4A) when the endoscope 2 having a large diameter is connected to the camera head 5 is larger than the size of the subject image SI (FIG. 4B) when the endoscope 2 having a small diameter is connected to the camera head 5. In FIGS. 4A and 4B, the mask area MA is hatched.

Then, the detection area setting unit 962 executes the detection area setting process to be described below.

The detection area setting unit 962 sets all detection areas Ar1 (FIG. 4A and FIG. 4B) at the center of the subject image SI in the subject image SI recognized by the subject image determining unit 961. In the first embodiment, a plurality of detection areas Ar1 (60 (=6×10) in the examples of FIG. 4A or FIG. 4B) are set in a matrix form. Here, the detection area setting unit 962 changes an area of all of a plurality of detection areas Ar1 by changing an area of each of the detection areas Ar1 based on the size of the subject image SI determined by the subject image determining unit 961 without changing the number of detection areas Ar1 (60 in the examples of FIG. 4A or FIG. 4B). More specifically, the detection area setting unit 962 changes an area of all of a plurality of detection areas Ar1 (the area of each detection area Ar1) such that a ratio of all the detection areas Ar1 to the subject image SI is the same (such that the ratio becomes a first value) regardless of the size of the subject image SI determined by the subject image determining unit 961. In other words, the area of one detection area Ar1 or the area of all the detection areas Ar1 increases as the size of the subject image SI increases.

In the first embodiment, since a plurality of detection areas Ar1 are set, the detection processing unit 93 executes the detection process of each detection area Ar1.

The evaluation value calculating unit 963 calculates the evaluation value of the image included in all the detection areas Ar1 based on the detection information (the detection information for each detection area Ar1) output from the detection processing unit 93.

Specifically, the evaluation value calculating unit 963 calculates an "evaluation value for the autofocus process" for evaluating the focused state of the subject image SI included in all of a plurality of detection areas Ar1 based on the detection information (for example, the contrast and the frequency components) output from the detection processing unit 93. Further, the evaluation value calculating unit 963 calculates an "evaluation value for brightness adjustment" for changing brightness of the captured image CI to reference brightness based on the detection information (for example, the average luminance value) output from the detection processing unit 93. Four brightness parameters, that is, an exposure time of each pixel in the imaging element 541, an analog gain multiplied by the signal processing unit 542, a digital gain multiplied by the image processing unit 92, and a light quantity of light supplied from the light source device 3 to the endoscope 2 may be used as the evaluation value for the brightness adjustment. Further, the evaluation value calculating unit 963 calculates an "evaluation value for white balance adjustment" based on the detection information output from the detection processing unit 93. A gain by which the RGB value is multiplied in the white balance adjustment process by the image processing unit 92 may be used as the evaluation value for the white balance adjustment. The evaluation value calculating unit 963 calculates an "evaluation value for an object recognition process" based on the detection information output from the detection processing unit 93. A degree of similarity to a template used in an object recognition process (for example, pattern matching) may be used as the evaluation value for the object recognition process. Further, the evaluation value calculating unit 963 calculates an "evaluation value for a shake compensation process" based on the detection information output from the detection processing unit 93. A deviation amount of the subject by camera shaking may be used as the evaluation value for the shake compensation process.

Based on the "evaluation value for the autofocus process" calculated by the evaluation value calculating unit 963 and the focus position detected by the lens position detecting unit 53, the lens controller 964 executes the AF process of moving the focus lens 511 to the focus position at which the subject image SI included in all the detection areas Ar1 becomes the focused state according to, for example, a hill climbing.

Based on the "evaluation value for the brightness adjustment" calculated by the evaluation value calculating unit 963, the brightness controller 965 executes the brightness adjustment process of controlling the operations of the imaging element 541, the signal processing unit 542, the image processing unit 92, and the light source device 3.

Specifically, the brightness controller 965 outputs the control signal to the imaging unit 54 via the first transmission cable 6, and uses the "evaluation value (exposure time) for the brightness adjustment" calculated by the evaluation value calculating unit 963 as the exposure time of each pixel of the imaging element 541. Further, the brightness controller 965 outputs the control signal to the imaging unit 54 via the first transmission cable 6, and uses the "evaluation value (analog gain) for the brightness adjustment" calculated by the evaluation value calculating unit 963 as the analog gain multiplied by the signal processing unit 542. Further, the brightness controller 965 outputs the control signal to the image processing unit 92, and uses the "evaluation value (digital gain) for the brightness adjustment" calculated by the evaluation value calculating unit 963 as the digital gain multiplied by the image processing unit 92. Further, the brightness controller 965 outputs the control signal to the light source device 3 via the third transmission cable 10, and uses the "evaluation value (light quantity) for the brightness adjustment" calculated by the evaluation value calculating unit 963 as the light quantity of the light supplied from the light source device 3 to the endoscope 2.

As the brightness adjustment process is executed as described above, the brightness of the captured image CI is changed to the reference brightness.

Based on the "evaluation value for the object recognition process" calculated by the evaluation value calculating unit 963, the object recognition processing unit 966 recognizes a predetermined object (for example, a treatment tool such as an electric scalpel, gauze, or the like) included in all of a plurality of detection areas Ar1.

The input unit 97 is configured using an operation device such as a mouse, a keyboard, or a touch panel, and receives an operation by a user.

The output unit 98 is configured using a speaker, a printer, or the like, and outputs various kinds of information.

The storage unit 99 stores a program executed by the control unit 96, information necessary for the process of the control unit 96, and the like.

Operation of Endoscope System

Next, an operation of the endoscope system 1 described above will be described.

Figure 5:
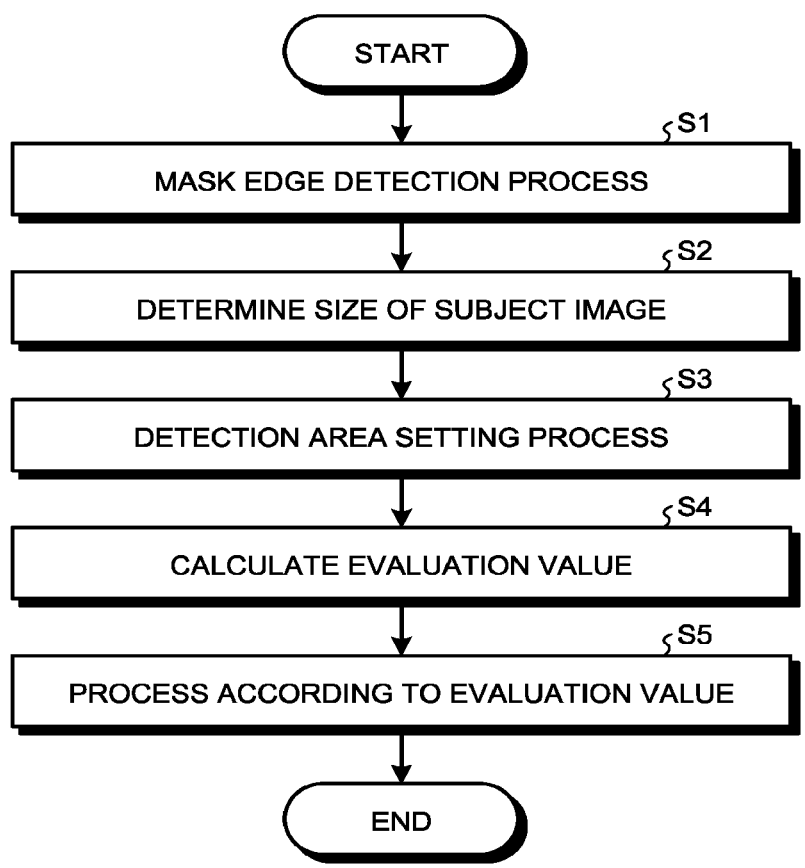
FIG. 5 is a flowchart illustrating an operation of the endoscope system.

FIG. 5 is a flowchart illustrating an operation of the endoscope system 1.

First, the edge processing unit 94 executes the mask edge detection process (Step S1).

After Step S1, the subject image determining unit 961 recognizes the subject image SI (pixel positions (coordinate values)) surrounded by a plurality of boundary points BP based on a plurality of boundary points BP (pixel positions (coordinate values) recognized in Step S1, and determines the size of the subject image SI (for example, the diameter of the subject image SI) (Step S2).

After Step S2, the detection area setting unit 962 executes the detection area setting process based on the determination result in Step S2 (Step S3).

After Step S3, the evaluation value calculating unit 963 calculates the evaluation values of the image included in all the detection areas Ar1 (the "evaluation value for the auto-focus process", the "evaluation value for the brightness adjustment", the "evaluation value for the white balance adjustment", the "evaluation value for the object recognition process", and the "evaluation value for the shake compensation process") based on the detection information (detection information of each detection area Ar1) output from the detection processing unit 93 (Step S4).

After Step S4, the control device 9 executes the processes corresponding to the evaluation value calculated in Step S4 (the AF process, the brightness adjustment process, the white balance adjustment process, the object recognition process, and the shake compensation process) (Step S5).

According to the first embodiment described above, the following effects are obtained.

The endoscope system 1 according to the first embodiment determines the size of the subject image SI in the captured image CI and changes the area of all the detection areas Ar1 based on the determination result.

Therefore, for example, when the endoscope 2 having a large diameter is connected to the camera head 5, all of a plurality of detection areas Ar1 are unlikely to have an extremely small area as compared with the subject image SI. Further, even if the size of the subject image SI is different, it is possible to set a ratio of a plurality of detection areas Ar1 to the subject image SI to a first value. Therefore, according to the endoscope system 1 according to the first embodiment, there is an effect in that it is possible to obtain the constant detection accuracy even when various endoscopes having different diameter sizes are used.

In particular, since a plurality of detection areas Ar1 are set, the detection accuracy may be improved by executing the detection process in each of a plurality of detection areas Ar1. In other words, even when various endoscopes having different diameter sizes are used, the high detection accuracy may be obtained, and various kinds of processes (the AF process, the brightness adjustment process, the white balance adjustment process, the object recognition process, and the shake compensation process) may be executed with a high degree of accuracy based on the highly accurate evaluation value.

In the endoscope system 1 according to the first embodiment, a plurality of boundary points BP are detected through the mask edge detection process, and the size of the subject image SI in the captured image CI is determined based on the boundary points BP. Therefore, the position and the size of the subject image SI may be accurately determined, and the detection area Ar1 may be set in the subject image SI with a high degree of accuracy.

Further, in the endoscope system 1 according to the first embodiment, even if the size of the subject image SI is different, the number of detection areas Ar1 is not changed. In other words, since the detection process is executed with the same number of detection areas Ar1 even if the size of the subject image SI is different, there is no need to install a plurality of detection processing units 93 depending on the size of the subject image SI, and the detection process may be executed with a simple configuration.

Second Embodiment

Next, a second embodiment will be described.

In the following description, the same reference numerals are assigned to components similar to those of the first embodiment, and detailed description thereof will be omitted or simplified.

Figure 6:
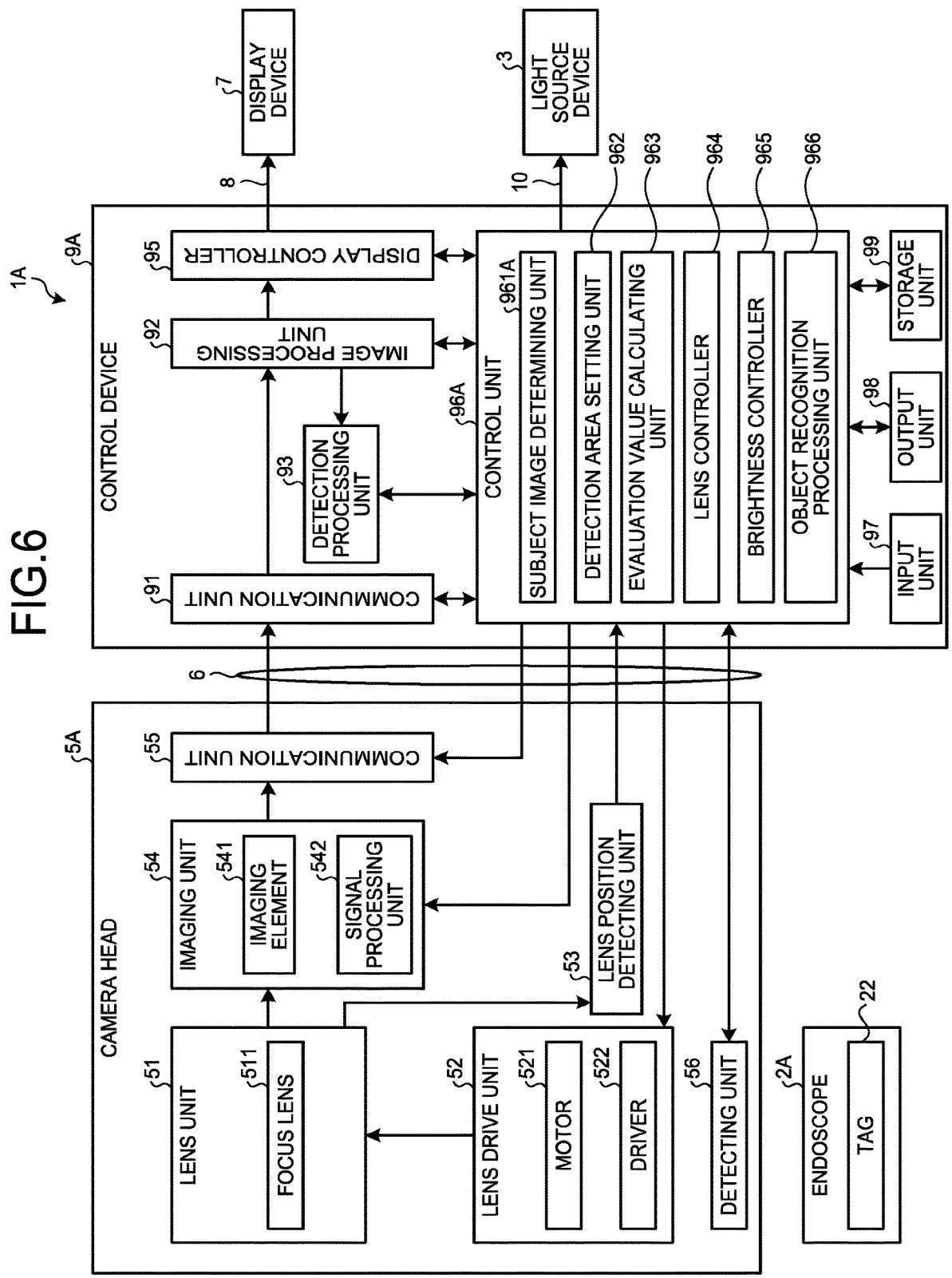
FIG. 6 is a diagram illustrating a schematic configuration of an endoscope system according to a second embodiment.

FIG. 6 is a block diagram corresponding to FIG. 2 and illustrating a configuration of an endoscope system 1A according to the second embodiment.

In the endoscope system 1 according to the first embodiment described above, the mask edge detection process is executed, and the size of the subject image SI is determined from a plurality of boundary points BP obtained by the mask edge detection process.

On the other hand, in the endoscope system 1A according to the second embodiment, identification information of the endoscope 2A is acquired from an endoscope 2A connected to a camera head 5A, and the size of the subject image SI is determined from the acquired identification information.

Specifically, in the endoscope 2A according to the second embodiment, a tag 22 is added to the endoscope 2 described in the first embodiment as illustrated in FIG. 6.

The tag 22 is constituted by, for example, a radio frequency identification (RFID) tag or the like and is installed in the eyepiece unit 21 or the like. Further, the tag 22 records identification information specific to the endoscope 2A.

In the camera head 5A according to the second embodiment, a detecting unit 56 is added to the camera head 5 described in the first embodiment as illustrated in FIG. 6.

The detecting unit 56 is constituted by, for example, an RFID detection circuit or the like, and acquires the identification information recorded in the tag 22 under the control of a control device 9A (a control unit 96A). Then, the detecting unit 56 outputs the acquired identification information to the control unit 96A via the first transmission cable 6.

Further, in the control device 9A according to the second embodiment, as illustrated in FIG. 6, the edge processing unit 94 is omitted from the control device 9 described in the first embodiment, and the control unit 96A is employed instead of the control unit 96.

Here, the storage unit 99 according to the second embodiment stores relevant information in which each piece of identification information of different endoscopes is associated with the size of the subject image SI included in the captured image CI captured by the imaging unit 54 in a state in which the endoscope is connected to the camera head 5A as information necessary for the process of the control unit 96A.

In the control unit 96A, a subject image determining unit 961A is employed instead of the subject image determining unit 961 for the control unit 96 described in the first embodiment.

The subject image determining unit 961A outputs the control signal to the detecting unit 56 via the first transmission cable 6 and causes the identification information recorded in the tag 22 to be acquired. Then, based on the relevant information stored in the storage unit 99, the subject image determining unit 961A determines the size of the subject image SI associated with the same identification information as the acquired identification information.

Further, an operation of the endoscope system 1A differs in that Step S1 is not executed as the operation of the endoscope system 1 described in the first embodiment, and the subject image determining unit 961A determines the size of the subject image SI in Step S2 as described above.

Even in a case in which the endoscope system 1A is configured as in the second embodiment described above, effects similar to those of the first embodiment are obtained.

Other Embodiments

The forms for carrying out the present disclosure have been described until now, but the present disclosure is not limited only by the first and second embodiments.

FIG. 7 is a diagram illustrating a modified example of the first and second embodiments.

In the first and second embodiments, when a part (for example, an enlarged area Ar2 illustrated in FIG. 7) of the captured image CI (the subject image SI) is displayed on the entire screen of the display device 7 (when an enlargement/reduction process is executed), the detection area Ar1 may be set as described below.

In other words, an area of each of a plurality of detection areas Ar1 (the area of each detection area Ar1) is changed such that the ratio of all the detection areas Ar1 to the enlarged area Ar2 is a first value, and a plurality of changed detection area Ar1 are set at the center of enlarged area Ar2.

Figure 8A:
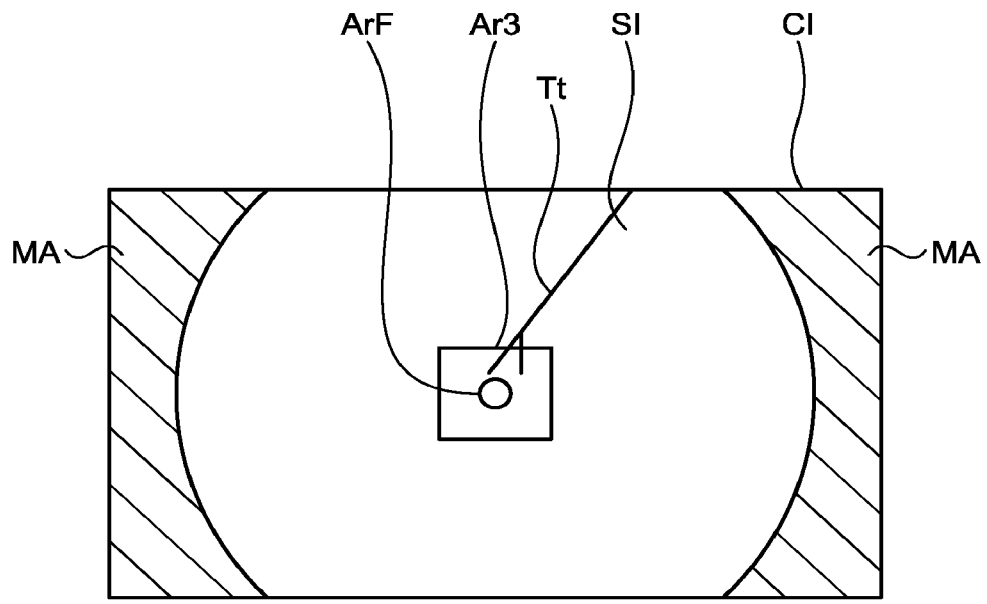
FIG. 8A is a diagram illustrating a modified example of the first and second embodiments.
Figure 8B:
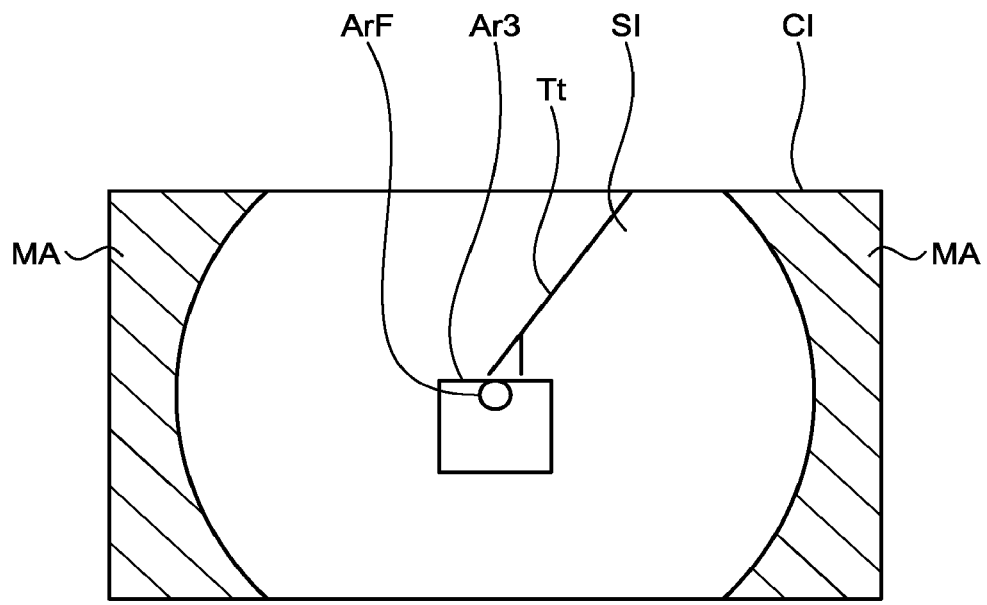
FIG. 8B is a diagram illustrating a modified example of the first and second embodiments.
Figure 9A:
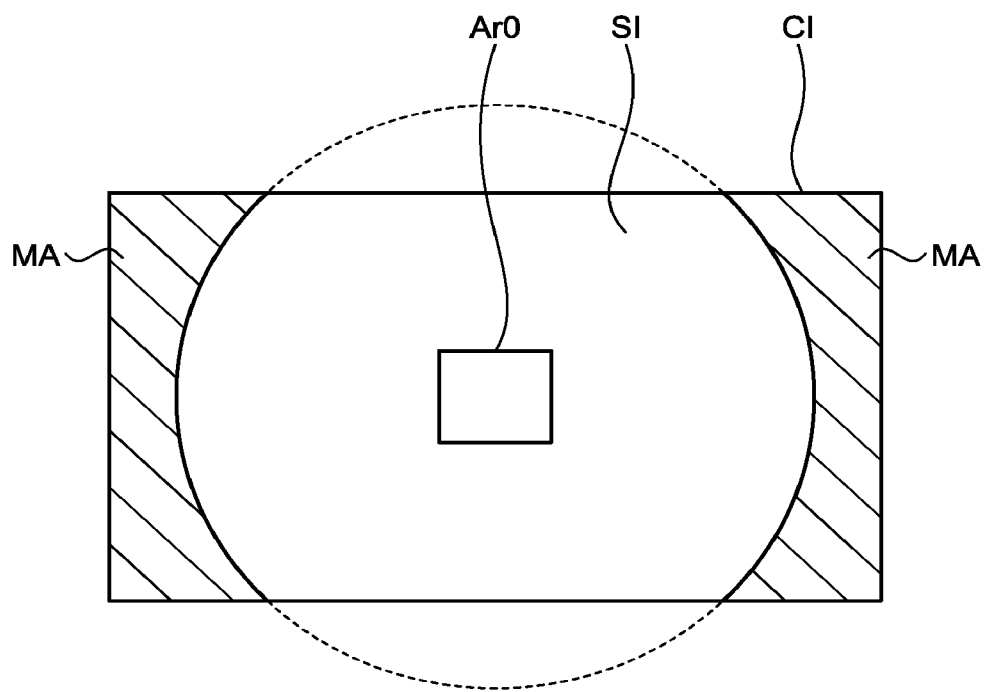
FIG. 9A is a diagram for describing a problem in an endoscope system according to a related art.
Figure 9B:
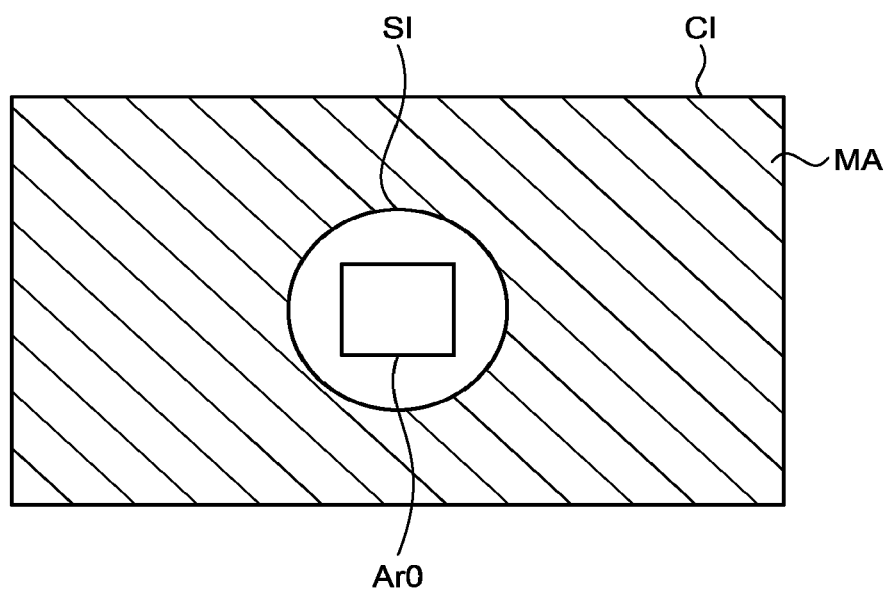
FIG. 9B is a diagram for describing a problem in an endoscope system according to a related art.

FIGS. 8A and 8B are diagrams illustrating a modified example of the first and second embodiments. Specifically, FIGS. 8A and 8B illustrate captured images CI in which a treatment tool Tt such as forceps is shown in the subject image SI.

By the way, as illustrated in FIG. 8A or FIG. 8B, the treatment tool Tt such as forceps often enters from an upper part in a field of view (an upper side in FIGS. 8A and 8B). Further, for example, when a detection area Ar3 is set at the center of the subject image SI as illustrated in FIG. 8A, a distal end of the treatment tool Tt such as forceps entering from the upper part of the field of view is likely to enter the detection area Ar3. In other words, if the detection process is executed based on the image including the treatment tool Tt in the detection area Ar3, the detection accuracy deteriorates. As a result, for example, an area of interest ArF (FIG. 8A) to be observed is unable to become the focused state or be adjusted to desired brightness.

In this regard, as illustrated in FIG. 8B, the detection area Ar3 is set slightly below the center of the subject image SI. If the detection area Ar3 is set in this manner, it is difficult for the distal end of the treatment tool Tt such as forceps entering from the upper part in the field of view to enter the detection area Ar3. Therefore, for example, the area of interest ArF (FIG. 8B) to be observed may become the focused state or be adjusted to the desired brightness.

In the first and second embodiments, all a plurality of detection areas Ar1 may be set slightly below the center of the subject image SI in the subject image SI.

In the first and second embodiments, a shape of an individual detection area Ar1 and a shape of all a plurality of detection areas Ar1 are rectangular shapes, but the present disclosure is not limited thereto and may be other shapes. Further, the detection areas Ar1 are adjacent to each other, but the present disclosure is not limited thereto, and the detection areas Ar1 may be spaced apart from one another. Further, even if the size of the subject image SI is different, the number of detection areas Ar1 is not changed, but the present disclosure is not limited thereto, and if the area of all of a plurality of detection areas Ar1 is changed, the number of detection areas Ar1 may be changed.

In the first and second embodiments, the same detection areas Ar1 are set when the detection processes for calculating the "evaluation value for the autofocus process", the "evaluation value for the brightness adjustment", the "evaluation value for the white balance adjustment", the "evaluation value for the object recognition process", and the "evaluation value for the shake compensation process" are performed, but the present disclosure is not limited thereto, and the detection areas Ar1 may be set such that at least one detection area Ar1 is different.

In the first and second embodiments, the detection process may be executed excluding the detection area Ar1 including the object recognized by the object recognition process among a plurality of detection areas Ar1.

In the first and second embodiments, at least a part of the configuration in which the control device 9 or 9A is installed may be installed outside the control device 9 or 9A (for example, the camera head 5 or 5A, the connector CN1 or CN2, or the like).

In the first and second embodiments, the endoscope system 1 and 1A may be used as an endoscope system which is used in industrial fields and used for observing a subject inside such as a machine structure.

An endoscope system according to the present disclosure determines a size of a subject image in a captured image and changes an area of the entire detection area based on a determination result.

Thus, for example, when an endoscope having a large diameter is connected to an imaging device, a detection area does not become an extremely small area as compared with the subject image. Further, even when the size of the subject image is different, it is possible to set a ratio of the entire detection area to the subject image to a substantially constant ratio. Therefore, according to the endoscope system according to the present disclosure, it is possible to obtain a constant detection accuracy even in a case in which various endoscopes having different diameter sizes are used.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An endoscope system comprising:
an imaging device detachably connected to an eyepiece of an endoscope inserted into a subject, the endoscope taking a subject image inside the subject from a distal end thereof, and the imaging device being configured to capture the subject image taken by the endoscope; and
processing circuitry configured to
determine a diameter size of the subject image in a captured image captured by the imaging device;
set, in the captured image captured by the imaging device, a detection area for performing a detection process of the subject, by setting a size of the detection area such that a ratio of the size of the detection area to the determined diameter size of the subject image becomes same based on the determined diameter size of the subject image; and
execute, based on an image in the detection area in the captured image, the detection process for calculating an evaluation value of the image in the detection area having the set size.

2. The endoscope system according to claim 1, wherein the processing circuitry is configured to:
detect a boundary point between the subject image included in the captured image and a mask area other than the subject image based on a luminance signal of each pixel in the captured image; and
determine the diameter size of the subject image in the captured image based on the detected boundary point.

3. The endoscope system according to claim 1, wherein the processing circuitry is configured to:
detect a type of the endoscope attached to the imaging device; and
determine the diameter size of the subject image in the captured image based on the detected type of the endoscope.

4. The endoscope system according to claim 1, wherein the detection process calculates the evaluation value for at least one of an autofocus process, brightness adjustment, white balance adjustment, an object recognition process, and a shake compensation process.

5. The endoscope system according to claim 1, wherein the processing circuitry is configured to:
set a plurality of detection areas; and
change each size of an area of each detection area of the plurality of detection areas, without changing number of the plurality of detection areas, based on the determined diameter size of the subject image.

6. The endoscope system according to claim 1, wherein the processing circuitry is configured to set the detection area in the subject image.

7. An endoscope system comprising:
an imaging device detachably connected to an eyepiece of an endoscope inserted into a subject, the endoscope taking a subject image inside the subject from a distal end thereof, and the imaging device being configured to capture the subject image taken by the endoscope; and
processing circuitry configured to
determine a size of the subject image in a captured image captured image based on a diameter size of the subject image;
set, in the captured image captured by the imaging device, a detection area for performing a detection process of the subject, by setting a size of the detection area such that a ratio of the size of the detection area to the determined size of the subject image becomes same based on the determined size of the subject image; and
execute, based on an image in the detection area in the captured image, the detection process for calculating an evaluation value of the image in the detection area having the set size.

8. The endoscope system according to claim 7, wherein the processing circuitry is configured to:
detect a boundary point between the subject image included in the captured image and a mask area other than the subject image based on a luminance signal of each pixel in the captured image; and
determine the size of the subject image in the captured image based on the detected boundary point.

9. The endoscope system according to claim 7, wherein the processing circuitry is configured to:
detect a type of the endoscope attached to the imaging device; and
determine the size of the subject image in the captured image based on the detected type of the endoscope.

10. The endoscope system according to claim 7, wherein the detection process calculates the evaluation value for at least one of an autofocus process, brightness adjustment, white balance adjustment, an object recognition process, and a shake compensation process.

11. The endoscope system according to claim 7, wherein the processing circuitry is configured to:
set a plurality of detection areas; and
change each size of an area of each detection area of the plurality of detection areas, without changing number of the plurality of detection areas, based on the determined size of the subject image.

12. The endoscope system according to claim 7, wherein the processing circuitry is configured to set the detection area in the subject image.

13. An endoscope system comprising:
an imaging device detachably connected to an eyepiece of an endoscope inserted into a subject, the endoscope taking a subject image inside the subject from a distal end thereof, and the imaging device being configured to capture the subject image taken by the endoscope; and
processing circuitry configured to
determine a size of the subject image in a captured image captured by the imaging device, the subject image in the captured image being round;
set, in the captured image captured by the imaging device a detection area for performing a detection process of the subject, by setting a size of the detection area such that a ratio of the size of the detection area to the determined size of the subject image becomes same based on the determined size of the subject image; and execute, based on an image in the detection area in the captured image, the detection process for calculating an evaluation value of the image in the detection area having the set size.

14. The endoscope system according to claim 13, wherein the processing circuitry is configured to:
   detect a boundary point between the subject image included in the captured image and a mask area other than the subject image based on a luminance signal of each pixel in the captured image; and
   determine the size of the subject image in the captured image based on the detected boundary point.

15. The endoscope system according to claim 13, wherein the processing circuitry is configured to:
   detect a type of the endoscope attached to the imaging device; and
   determine the size of the subject image in the captured image based on the detected type of the endoscope.

16. The endoscope system according to claim 13, wherein the detection process calculates the evaluation value for at least one of an autofocus process, brightness adjustment, white balance adjustment, an object recognition process, and a shake compensation process.

17. The endoscope system according to claim 13, wherein the processing circuitry is configured to:
   set a plurality of detection areas; and
   change each size of an area of each detection area of the plurality of detection areas, without changing number of the plurality of detection areas, based on the determined size of the subject image.

18. The endoscope system according to claim 13, wherein the processing circuitry is configured to set the detection area in the subject image.

* * * * *